US011779745B2

(12) United States Patent
Stout et al.

(10) Patent No.: US 11,779,745 B2
(45) Date of Patent: Oct. 10, 2023

(54) FLUSH ENHANCING MALE LUER TIP DESIGN FOR SYRINGES AND ANY LUER CONNECTOR

(71) Applicant: Becton, Dickinson and Company, Franklin Lakes, NJ (US)

(72) Inventors: Marty L. Stout, South Jordan, UT (US); Jonathan Karl Burkholz, Salt Lake City, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/397,268

(22) Filed: Apr. 29, 2019

(65) Prior Publication Data

US 2019/0247641 A1  Aug. 15, 2019

Related U.S. Application Data (62) Division of application No. 15/388,476, filed on Dec. 22, 2016, now Pat. No. 10,272,237, which is a
(Continued)

(51) Int. Cl.
*A61M 39/10* (2006.01)
*A61M 5/178* (2006.01)
(Continued)

(52) U.S. Cl.
CPC ............ *A61M 39/10* (2013.01); *A61M 5/178* (2013.01); *A61M 25/0606* (2013.01);
(Continued)

(58) Field of Classification Search
CPC ............ A61M 5/3134; A61M 25/0068; A61M 2025/0073; A61M 39/10;
(Continued)

(56) References Cited

U.S. PATENT DOCUMENTS

| 4,869,103 A | 9/1989 | Jerman |
| 5,312,048 A | 5/1994 | Steingass et al. |

(Continued)

FOREIGN PATENT DOCUMENTS

| CN | 103492008 A | 1/2014 |
| JP | 2002503991 A | 2/2002 |

(Continued)

OTHER PUBLICATIONS

PCT International Preliminary Reporton Patentability in PCT/US2013/041810, dated Dec. 4, 2014, 7 pages.
PCT International Search Report and Written Opinion in PCT/US2013/041810, dated Oct. 31, 2013, 10 pgs.

*Primary Examiner* — Kami A Bosworth
(74) *Attorney, Agent, or Firm* — Servilla Whitney LLC (57) ABSTRACT

A luer connection device is disclosed having a housing including a side wall having an inside surface defining a lumen with a central axis, an proximal end, and a distal end including a male luer tip within the lumen having a central flow diverter extending outwardly from the central axis to direct a fluid to a circumferential dead space distal to the male luer tip. A luer connection device is also disclosed having a flow expansion channel disposed in the lumen tapering outward from the wall of tubular housing and partially extending along a longitudinal axis from the tip opening toward the base opening for increasing mixing and flow through a circumferential dead space in the fluid path distal to the male luer tip.

13 Claims, 8 Drawing Sheets

Related U.S. Application Data division of application No. 13/476,357, filed on May 21, 2012, now Pat. No. 9,616,214.

(51) Int. Cl.
    *A61M 25/06*     (2006.01)
    *A61M 39/22*     (2006.01)
    *A61M 25/00*     (2006.01)

(52) U.S. Cl.
    CPC ..... *A61M 39/22* (2013.01); *A61M 2025/0062* (2013.01); *A61M 2025/0073* (2013.01); *A61M 2039/1077* (2013.01); *A61M 2039/1094* (2013.01); *A61M 2039/229* (2013.01)

(58) Field of Classification Search
    CPC ............. A61M 2039/1077; A61M 2039/1094; A61M 2206/10; A61M 2206/11; A61M 2206/12; A61M 2206/14; A61M 2206/16; A61M 2206/18; A61M 2206/20
See application file for complete search history.

(56) References Cited

U.S. PATENT DOCUMENTS

| | | |
|---|---|---|
| 5,354,288 A | 10/1994 | Cosgrove et al. |
| 5,775,671 A | 7/1998 | Cote, Sr. |
| 6,830,563 B1 | 12/2004 | Singer |
| 2003/0089797 A1 | 5/2003 | Buck |
| 2004/0210202 A1 | 10/2004 | Weinstein |
| 2007/0123834 A1 | 5/2007 | McDowall et al. |
| 2008/0091173 A1 | 4/2008 | Belley et al. |
| 2008/0287920 A1 | 11/2008 | Fangrow et al. |
| 2009/0143770 A1 | 6/2009 | Robinson et al. |
| 2011/0015582 A1 | 1/2011 | Fangrow, Jr. |
| 2011/0046570 A1 | 2/2011 | Stout et al. |
| 2011/0160662 A1 | 6/2011 | Stout et al. |
| 2011/0276035 A1 | 11/2011 | Fangrow, Jr. et al. |
| 2013/0331817 A1 | 12/2013 | Woehr |

FOREIGN PATENT DOCUMENTS

| | | |
|---|---|---|
| WO | 2012009028 A1 | 1/2012 |
| WO | 2012113865 A1 | 8/2012 |

FLUSH ENHANCING MALE LUER TIP DESIGN FOR SYRINGES AND ANY LUER CONNECTOR

CROSS-REFERENCE TO RELATED APPLICATIONS

This application is a divisional of U.S. patent application Ser. No. 15/388,476, filed on Dec. 22, 2016, now U.S. Pat. No. 10,272,237 issued on Apr. 30, 2019, which is a divisional of U.S. patent application Ser. No. 13/476,357 filed on May 21, 2012, now U.S. Pat. No. 9,616,214 issued on Apr. 11, 2017, the entire disclosure of which is hereby incorporated by reference herein.

TECHNICAL FIELD

An aspect of the invention relates generally to a luer connection device, and more particularly to a luer connection device a housing including a side wall having an inside surface defining a lumen with a central axis, a proximal end, and a distal end, the side wall comprising a male luer tip, and the lumen having a central flow diverter extending outwardly from the central axis to direct a fluid to a circumferential dead space distal to the male luer tip. Another aspect of the invention relates a luer connection device having a flow expansion channel disposed in the side wall of the housing tapering outward from the wall of tubular housing and partially extending along a longitudinal axis from the tip opening toward the base opening for increasing mixing and flow through a circumferential dead space in the fluid path distal to the male luer tip. Yet another aspect of the invention relates a luer connection device having both a central flow diverter and a flow expansion channel disposed in the side wall of the housing.

BACKGROUND

Vascular Access Devices (VADs) are commonly used therapeutic devices and include intravenous catheters, syringes, extension sets, stop cocks, tubing, high pressure extension tubing, and needleless access devices. The operation of VADs is often compromised or completely prevented by the occurrence of thrombus formation. Thrombosis is the development of a blood clot within a vessel and/or vascular access device. If not properly maintained, VADs can become occluded. To ensure VADs are used properly and do not become occluded, standards of practice have been developed. These standards include a cleaning procedure, which is commonly referred to as a flush procedure. The purpose of flushing is to clean the accumulated residue from deadspace located between male and female luer connections. The common flushing practice creates a turbulent flow during flushing to promote a "scrubbing" effect in the lumen and at the tip of the catheter.

The effectiveness of the flushing procedure in intravenous therapy is related to the risk of microbial colonization and potential Catheter Related Bloodstream Infection (CRBSI). Standard male luer tip geometries result in a circumferential "dead space" in the fluid path distal to the male luer tip that is inherently difficult to flush. After standard flushing procedures, an excess amount of blood can be left in this difficult to flush region, thereby increasing the risk of microbial colonization. Thus, the greater the amount of blood and residue remaining in the catheter system, the higher the risk for infection and complications related to infection. Clinicians can attempt to improve flushing with pulsatile techniques that may encourage mixing and better flush results. Due to these inherent challenges, there is a need for a device that improves the outcome of a flush procedure by removing the blood and residue build up found in the circumferential "dead space".

SUMMARY

Embodiments of the present invention are directed to a luer connection device including a housing having a side wall with an inside surface defining a lumen with a central axis, a proximal end, and a distal end, the side wall comprising a male luer tip, and the lumen having a passageway therethrough providing fluid communication between the proximal end and the distal end. The side wall comprising a male luer tip and the lumen at or near the distal end including a central flow diverter extending outwardly from the central axis to direct a fluid to a circumferential dead space distal to the male luer tip.

In one or more embodiments, the luer connection device may also include at least one flow expansion channel for increasing flow and mixing a fluid through a circumferential dead space in the fluid path distal to the male luer tip. The flow expansion channel can be configured to extend in a straight taper outwardly from the central axis of the lumen. In one or more embodiments, the flow expansion channel may be configured to extend in a rotational taper outwardly from the central axis of the lumen. The flow expansion channel can be located upstream from the flow diverter.

The proximal end of the luer connection device can be integrally connected to a vascular access device. The vascular access device may be a syringe, extension set, intravenous set, stop cock, tubing, high pressure extension tubing, or needleless access device. The luer connection device can be removably connected to a vascular access device.

In one or more embodiments, the central flow path diverter comprises a plurality of vanes. In one or more embodiments, the plurality of vanes may have a tapered leading edge and tapered tailing edge to minimize drag and reduce resistance. The tapered leading edge may be configured to create a smooth entrance of fluid and the tapered tailing edge is configured to create a sharp exit for producing turbulent fluid flow upon exiting the flow diverter.

In one or more embodiments, the plurality of vanes may be configured to extend straight outwardly from the central axis of the lumen to the side wall. In one variation, the plurality of vanes extends outwardly from the central axis of the lumen in a curved configuration. At least one edge of the plurality of vanes can have a ramped angled surface to create a greater angle of incidence. The central flow path diverter can be configured in various shapes, for example, in a cross, rectangle, star, triangle, oval, spiral, twisting or helical formation.

An aspect invention pertains to a luer connection device including a housing having a side wall with an inside surface defining a lumen, a proximal end and a distal end including a distal wall with an elongate male luer tip extending in a distal direction therefrom having a passageway therethrough providing fluid communication between the proximal end and the distal end; and a flow expansion channel being disposed in the lumen tapering outward from the wall of tubular housing and partially extending along a longitudinal axis from the tip opening toward the base opening for increasing mixing and flow through a circumferential dead space in the fluid path distal to the male luer tip.

The proximal end can be integrally connected to a vascular access device. The vascular access device may be a syringe, extension set, intravenous set, stop cock, tubing, high pressure extension tubing, or needleless access device. In one or more embodiments, the syringe is a pre-filled flush syringe. The luer connection device can be removably connected to a vascular access device.

The flow expansion channel can be configured to extend in a straight taper outwardly from the central axis of the lumen. The flow expansion channel may be configured to extend in a rotational taper outwardly from the central axis of the lumen. The flow expansion channel may be configured to scallop outwardly from the central axis of the lumen. In one or more embodiments, the flow expansion channel is located at the distal end and projects axially in a proximal direction towards the proximal end.

In one or more embodiments, the luer connection device also includes a flow diverter disposed in the lumen at or near the distal end of the male luer tip to direct the fluid flow to the periphery of a connecting female luer space upon application of force in the distal direction. The flow diverter can extend beyond the distal end of the housing. The flow diverter may be connected to the flow expansion channel. The flow expansion channel may be located upstream from the flow diverter.

In an embodiment, the flow diverter can direct fluid flow into the flow expansion channel. In another embodiment, the flow expansion channel directs fluid flow into the flow diverter.

In one or more embodiments, the flow expansion channel and flow diverter are both configured to extend in a straight taper towards the central axis of the lumen. In another embodiment, the flow expansion channel is configured to extend in a rotational taper towards the central axis of the lumen and flow diverter is configured to extend in a straight taper towards the central axis of the lumen. In yet another embodiment, the flow diverter is configured to extend in a rotational taper towards the central axis of the lumen and flow expansion channel is configured to extend in a straight taper towards the central axis of the lumen.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

Figure 1:
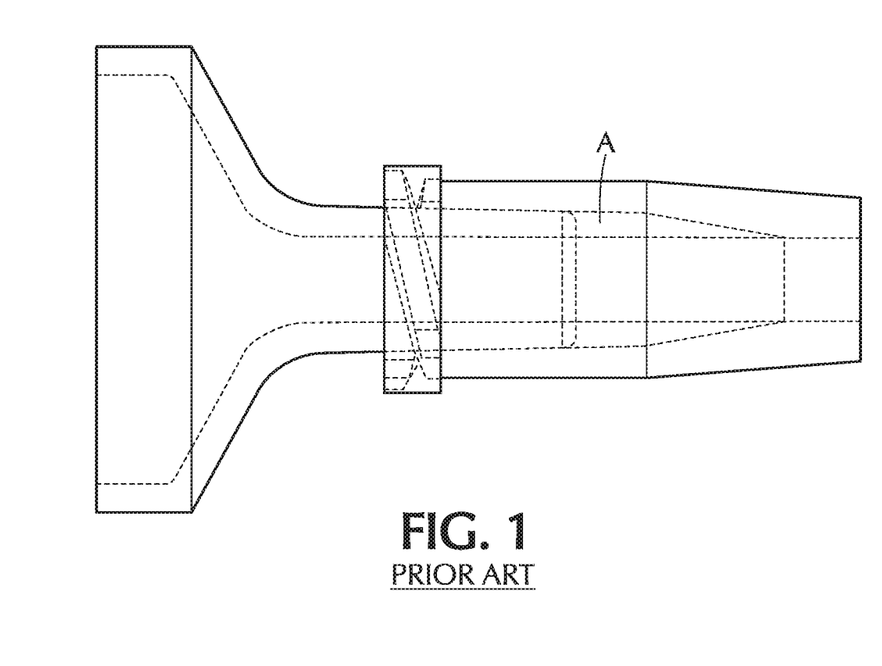
FIG. 1 shows a standard prior art luer connection device having a standard male luer tip straight central fluid path having zones of flow stagnation.

Many VADs have luer fittings which contain male luer tips. FIG. 1 shows zones of flow stagnation, depicted as "A", where blood-derived debris can typically form in a standard prior art luer connection device having a standard male luer tip straight central fluid path.

The present invention overcomes problems associated with known flushing techniques by providing a luer connection device having a male luer tip that effectively scrubs the blood, residue and other debris from deadspace located between male and female luer connections. The present invention provides a luer connection device having a male luer tip with internal geometry that promotes improved flushing of any male to female luer connection whether it is connecting to a catheter, extension set, IV set, IV access device or any connector that includes a male luer for connection to a female luer. The luer connection device may be a stand alone component or may be integrally connected to a vascular access device that requires enhanced flushing prior to being connected to the female luer connection and performing the flush procedure. The luer connection device of the present invention includes a male luer tip having a flow diverter 80 and/or flow channels 90 in a variety of forms to improve the removal of blood in the systems for a given flush volume. The present invention may also be useful for flushing needless IV access valves, such as BD Q-Syte™. The luer connection device of the present invention can be removably attached or integrally attached to a pre-filled flush syringe for improved clinical outcomes. The luer connection device of the present invention may also be used in combination with other CRBSI risk reducing features, including, antimicrobial solutions and cleaning and protection caps, to establish an improved practice for reducing CRSI risk associated with flushing an infusion system.

Figure 2:
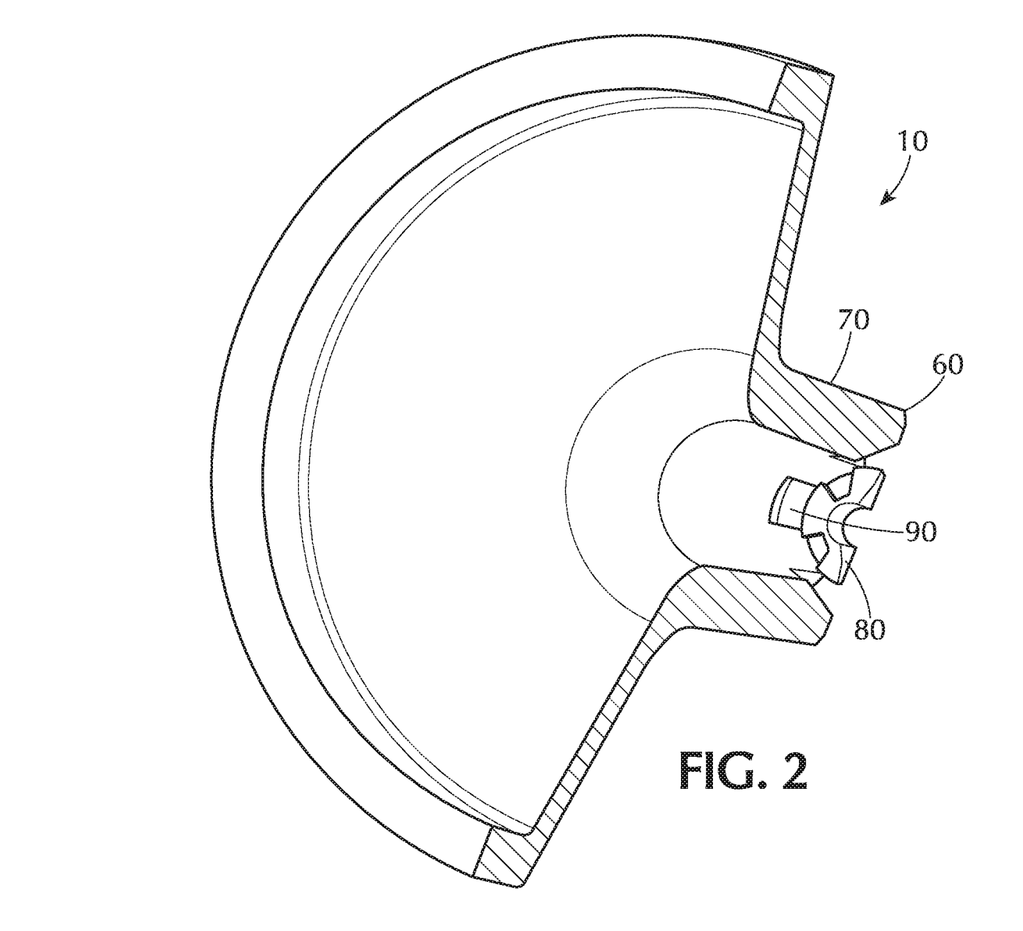
FIG. 2 is a cross-sectional view of the luer connection device having a flow diverter and flow expansion channel.
Figure 3:
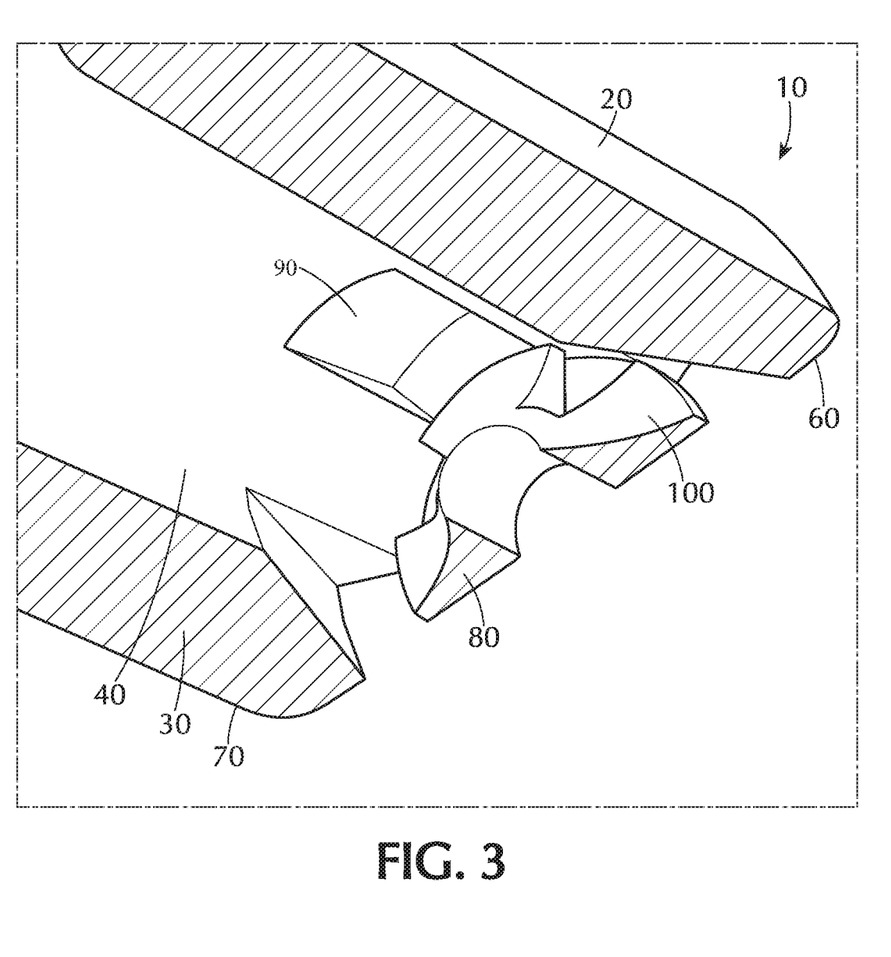
FIG. 3 is a cross-sectional view of the luer connection device having straight non-rotational flow expansion channels and rotational flow diverter.
Figure 4:
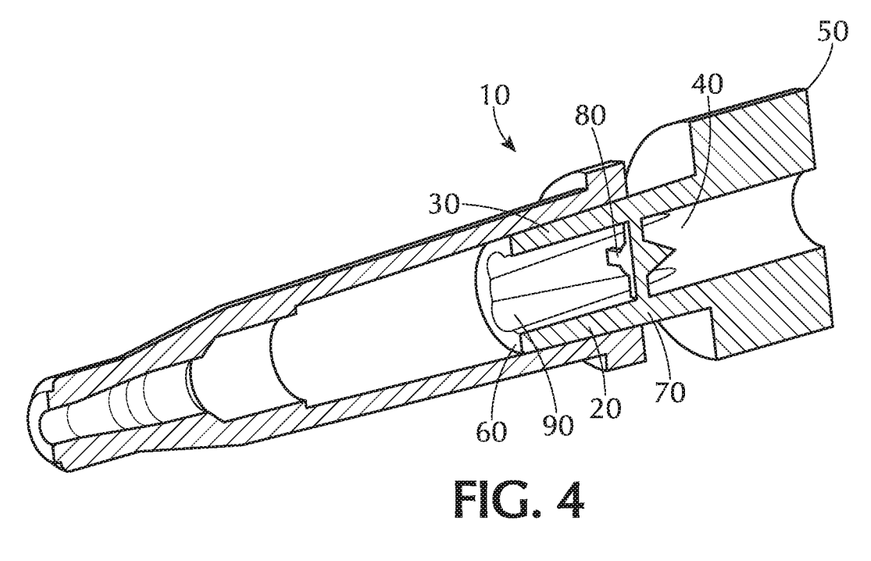
FIG. 4 is a cross-sectional of the luer connection device having straight non-rotational flow expanding channels.

FIGS. 2-4 illustrate an exemplary luer connection device 10 according to the present invention. Luer connection device 10 includes a housing 20 having a side wall 30 with an inside surface defining a lumen 40 with a central axis, a proximal end 50, and a distal end 60, the side wall 30 comprising a male luer tip 70, and the lumen having a passageway therethrough providing fluid communication between the proximal end 50 and the distal end 60 through which fluid, e.g. flush fluid, may be ejected. The side wall comprising a male luer tip 70 and the lumen at or near the distal end includes a central flow diverter 80 extending outwardly from the central axis to direct fluid flow to a peripheral circumferential dead space located distal to the male luer tip.

In one or more embodiments, the luer connection device 10 may also include at least one flow expansion channel 90 for increasing mixing and flow through circumferential dead space in the fluid path distal to the male luer tip. The flow expanding channel 90 increases mixing and flow through the "dead" space, thereby significantly improving the removal of the blood, medicine and/or other fluids and provide superior flushing. In the embodiment shown, flow expansion channel 90 is disposed on the interior surface of the housing lumen 40 and can be round, square, triangular, or a combination thereof, or any other suitable shape. Specifically, the flow expansion channel 90 is shown as a structure that projects outward from the side wall 30 of the housing lumen 40 and reduces the cross-sectional width of the lumen 40. The cross-sectional width of the interior surface of the lumen at the flow expansion channel is less than the cross-sectional width of the lumen at the remaining portions. It will be understood that the flow expansion channel 90 may be disposed at other locations along the interior surface of the side wall 30. In another variant, the flow expansion channel 90 may include a plurality of outwardly extending projections disposed along the axial length of the housing 20 and may be disposed at pre-defined intervals along the axial length. The flow expansion channels also extend longitudinally along the length of the lumen and may be disposed at intervals along the length of the lumen. In one or more embodiments, the flow expansion channels may be tapered. In one or more embodiments, the flow expansion channel 90 is configured to extend in a straight taper outwardly from the lumen 40 towards the central axis of the lumen. In one or more embodiments, the flow expansion channel 90 may be configured to extend in a rotational taper outwardly from the central axis of the lumen. In one or more embodiments, the flow expansion channel 90 is located upstream from the flow diverter 80.

It will be appreciated that the flow diverter 80 and/or flow expansion channel 90 is located within the interior surface of the lumen 40 forces fluid to peripheral space formed between the male and female luer connections. The central flow path diverter, alone or in combinations with the flow expansion channels, significantly improves the flushing and removal of fluid downstream from the luer tip by forcing the fluid to the periphery or the female luer space. Thus, the present invention improves flow based on flow expansion, disruptions of dead space creating features, and flow diversion outward.

In one or more embodiments, the proximal end 50 of the luer connection device 10 is integrally connected to a vascular access device. The vascular access device may be a syringe, extension set, intravenous set, stop cock, tubing, high pressure extension tubing, or needleless access device. In one or more embodiments, the luer connection device is removably connected to a vascular access device.

In one or more embodiments, the central flow path diverter comprises a plurality of vanes. As used herein, a vane can include any number of known internal dividers capable of manipulating the path of a liquid. Internal dividers may include louvers or tapered leading and tailing edges. The plurality of vaines create turbulence in the flow of flushing fluid to reduce the dead space which might otherwise form on the peripheral surface of the wall portion located between the male luer and female luer connection. In one or more embodiments of the present invention, the plurality of vanes may have a tapered leading edge and tapered tailing edge to minimize drag and reduce resistance. In one or more embodiments, the tapered leading edge may be configured to create a smooth entrance of fluid and the tapered tailing edge is configured to create a sharp exit for producing turbulent fluid flow upon exiting the flow diverter.

In one or more embodiments, the plurality of vanes may be configured to extend straight outwardly from the central axis of the lumen 40 to the side wall 30. In yet another embodiment, the plurality of vanes extend outwardly from the central axis of the lumen in a curved configuration. In one or more embodiments, at least one edge of the plurality of vanes has a ramped angled surface to create a greater angle of incidence.

The flow expansion channel and flow diverter of the present invention may have a variety of cross sectional geometries including, but not limited to, a cross, rectangle, star, triangle, oval, spiral, twisting or helical formation.

The present invention is also directed to a luer connection device 10 including a housing 20 having a side wall 30 with an inside surface defining a lumen 40, a proximal end 50 and a distal end 60 including a distal wall with an elongate male luer tip 70 extending in a distal direction therefrom having a passageway therethrough providing fluid communication between the proximal end 50 and the distal end 60; and a flow expansion channel 90 being disposed in the lumen 40 tapering outward from the wall of tubular housing 20 and partially extending along a longitudinal axis from the tip opening toward the base opening for increasing mixing and flow through a circumferential dead space in the fluid path distal to the male luer tip. The flow expanding channels increase mixing and flow through the "dead" space, thereby significantly improving the removal of the blood, medicine and/or other fluids and provide superior flushing.

In one or more embodiments, the proximal end 50 is integrally connected to a vascular access device. The vascular access device may be a syringe, extension set, intravenous set, stop cock, tubing, high pressure extension tubing, or needleless access device. In one or more embodiments, the syringe is a pre-filled flush syringe. In yet another embodiment, the luer connection device 10 of claim is removably connected to a vascular access device.

In one or more embodiments, the flow expansion channel is configured to extend in a straight taper outwardly from the central axis of the lumen. In yet another embodiment of the present invention, the flow expansion channel may be configured to extend in a rotational taper outwardly from the central axis of the lumen. In another embodiment, the flow expansion channel may be is configured to scallop outwardly from the central axis of the lumen.

In one or more embodiments, the flow expansion channel is located at the distal end and projects axially in a proximal direction towards the proximal end.

In one or more embodiments, the luer connection device 10 also includes a flow diverter 80 disposed in the lumen at or near the distal end of the male luer tip 70 to direct the fluid flow to the periphery of a connecting female luer space upon application of force in the distal direction. In one or more embodiments, the flow diverter 80 extends beyond the distal end of the housing 20. In one or more embodiments, the flow diverter 80 may be connected to the flow expansion channel 90. In one or more embodiments, the flow expansion channel 90 may be located upstream from the flow diverter 80.

In one or more embodiments, the flow diverter 80 directs fluid flow into the flow expansion channel 90. In another embodiment, the flow expansion channel 90 directs fluid flow into the flow diverter 80. In one or more embodiments, the flow diverter may merge into flow expansion channels.

Figure 5:
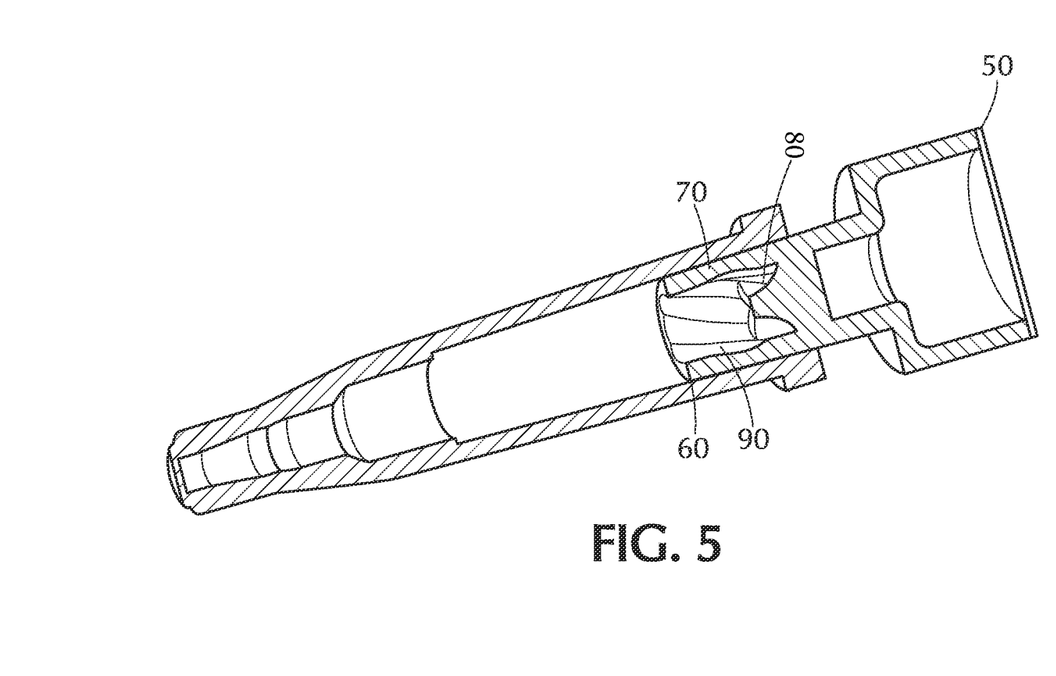
FIG. 5 is a cross-sectional of the luer connection device having rotational flow expansion channels.

It is envisioned that numerous combinations of flow expansion channels and central flow diverters are possible including, but not limited to, a straight or rotational flow expanding channels on the inner diameter of the male luer space. Straight or rotational central flow diverters having one or more flow channels are also within the scope of the present invention. In one embodiment of the present invention, the male luer tip may include a rotational flow expanding channels and a central, circulating flow diverter. As shown in FIG. 5, in some embodiments, the central flow diverter 80 is located upstream from the flow expansion channel 90.

FIG. 2 illustrates an exemplary luer connection device 10 having a flow expansion channel 90 and flow diverter 80 that are both configured to extend in a straight taper towards the central axis of the lumen. In another embodiment, the flow expansion channel is configured to extend in a rotational taper towards the central axis of the lumen and flow diverter 80 is configured to extend in a straight taper towards the central axis of the lumen. FIG. 5 illustrates an exemplary luer connection device 10 having a male luer tip with a rotational flow expansion channels and central flow diverters.

In yet another embodiment, the flow diverter is configured to extend in a rotational taper towards the central axis of the lumen and flow expansion channel is configured to extend in a straight taper towards the central axis of the lumen.

Blood-derived debris in the deadspace is dislodged by diverting the fluid flow to the periphery of the connecting female luer space during a flush procedure to increase mixing and turbulence in the dead space created by a male luer tip.

FIG. 3 illustrates an exemplary luer connection device 10 having straight non-rotational flow expansion channels and rotational flow diverter.

FIG. 4 illustrates an exemplary luer connection device 10 having straight non-rotational flow expanding channels.

FIG. 5 illustrates an exemplary luer connection device 10 having rotational flow expansion channels.

Figure 6:
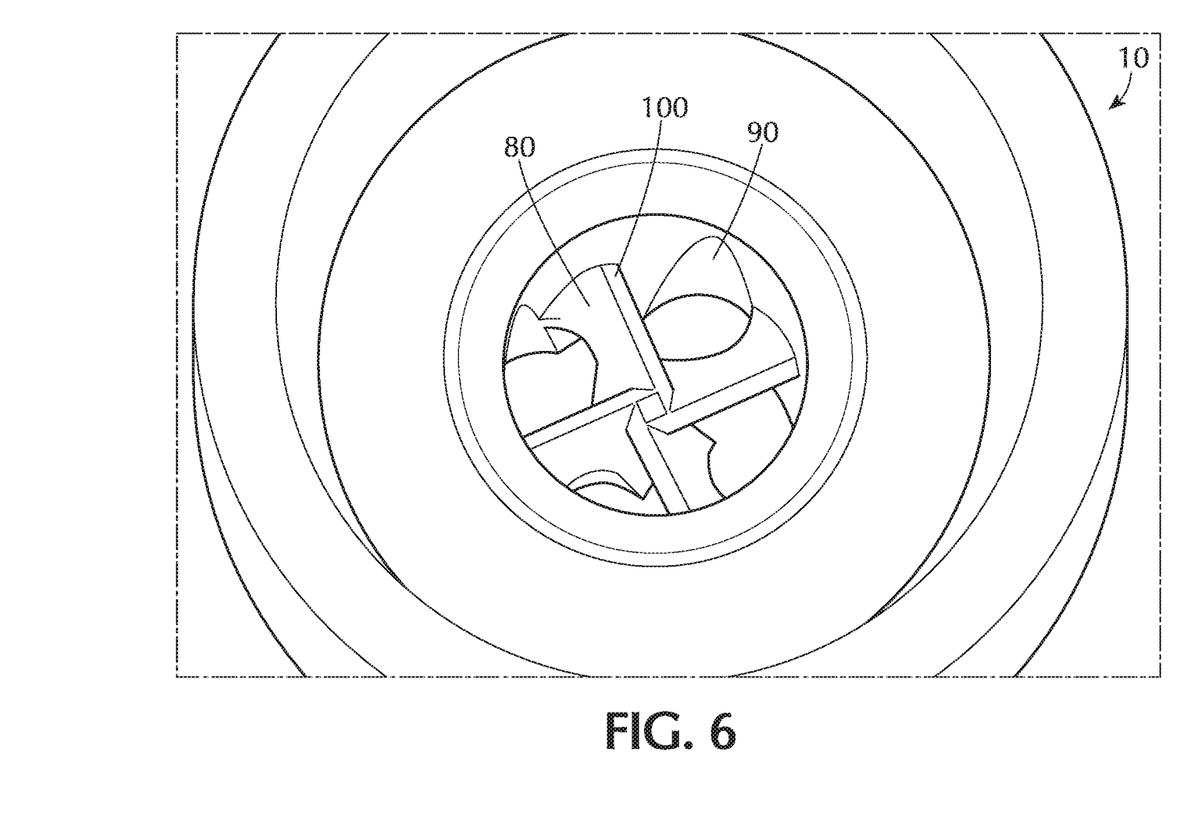
FIG. 6 shows a front view of the luer connection device having a straight non-rotational flow expansion channels and rotational diverter having ramped angled edges.

FIG. 6 shows a front view of the flow diverter located at the distal end 60. FIG. 6 illustrates an exemplary luer connection device 10 having a straight non-rotational flow expansion channels and rotational diverter having ramped angled edges.

Figure 7:
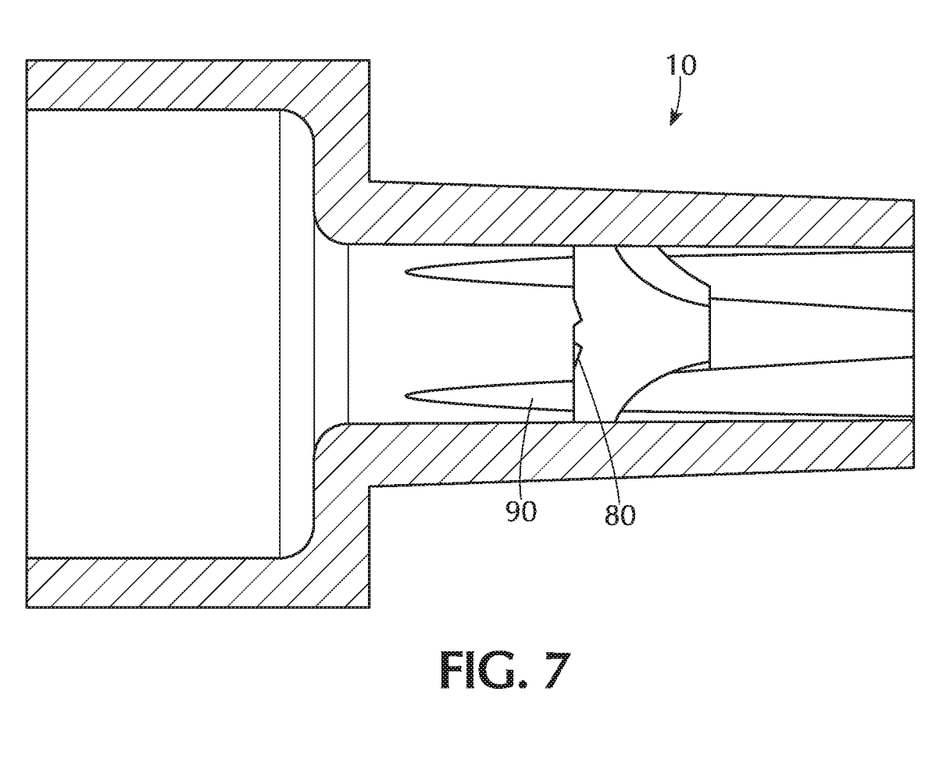
FIG. 7 shows a plan view of the luer connection device having a flow diverter and straight flow expansion channels.
Figure 8:
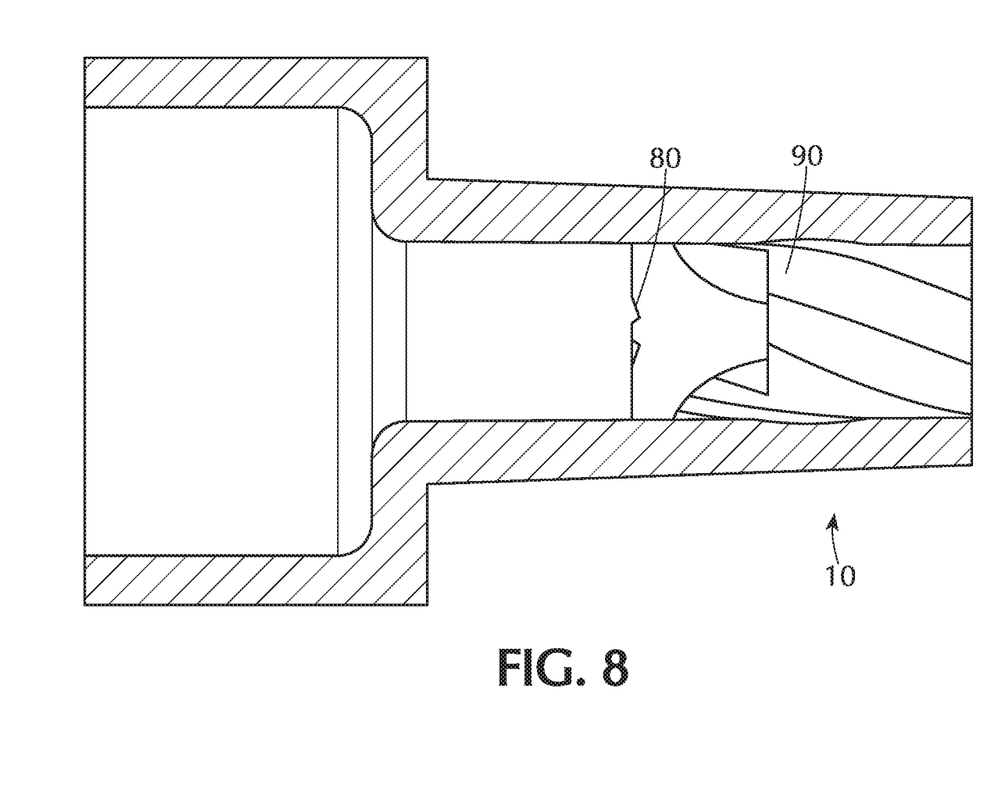
FIG. 8 shows a plan view of the luer connection device having a flow diverter and rotational flow expansion channels.

FIG. 7 illustrates an exemplary luer connection device 10 having a flow diverter and straight flow expansion channels. FIG. 8 shows a side view of luer connection device, illustrating how flow expansion channels 90 protrude/twist as it courses evenly and smoothly from proximal end 50 to distal end 60.

The purpose of the flow expanding channels is to increase mixing and flow through the "dead" space, thereby significantly improving the removal of the blood, medicine and/or other fluids and provide superior flushing.

The flow diverter can direct flow into deadspace located between a male and female luer connection so as to minimize the trapping of blood within the passageway.

Flow diverter 80 is provided within the male luer tip to force the fluid flow to the periphery of the connecting female luer space during a flush procedure to increase mixing and turbulence in the dead space created by a male luer tip between a male and female luer connection. This enhanced flushing results in a reduction in the risk of infection due to residual blood in the catheter system. The flow diverter 80 is integrally formed within male luer tip.

The tip has a flow expanding channel and flow diverter. The flow of flushing fluid then circulates radially outward through the flow diverter to the outer periphery of the tip into the deadspace.

The flush enhancing luer connection device of the present invention, with either flow expanding channels or a flow diverter, or a combination of the two, provides a significant improvement to the standard flush devices and procedures. This is accomplished by diverting the fluid flow to the periphery of the connecting female luer space during a flush procedure to increase mixing and turbulence in the dead space created by a male luer tip. This enhanced flushing results in a reduction in the risk of infection due to residual blood in the catheter system.

The dimensions of the luer connection device of the present invention can be made to comply with applicable standards and/or regulations, such as ISO standard 594.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A luer connection device comprising:
   a housing including a side wall having an inside surface defining a lumen with a central axis, a proximal end, and a distal end, the side wall comprising a male luer tip, and the lumen having a passageway therethrough providing fluid communication between the proximal end of the side wall and the distal end of the side wall;
   a central flow diverter configured to extend in a rotational taper towards the central axis of the lumen to direct a fluid to a circumferential dead space distal to the male luer tip; and
   at least one flow expansion channel disposed in the side wall of the housing configured to scallop outwardly and extend along a partial length of the lumen in a rotational taper outwardly from the central axis of the lumen, wherein the central flow diverter is connected to the at least one flow expansion channel.

2. The luer connection device of claim 1, wherein the central flow diverter is configured in a cross, rectangle, star, triangle, oval, spiral, twisting or helical formation.

3. The luer connection device of claim 1, wherein the central flow diverter has ramped angled edges.

4. The luer connection device of claim 1, wherein the proximal end is removably connected to a vascular access device.

5. The luer connection device of claim 4, wherein the vascular access device is a syringe, an extension set, an intravenous set, a stop cock, tubing, high pressure extension tubing or a needleless connector.

6. The luer connection device of claim 1, wherein the proximal end is integrally connected to a vascular access device.

7. The luer connection device of claim 6, wherein the vascular access device is a syringe, an extension set, an intravenous set, a stop cock, tubing, high pressure extension tubing or a needleless connector.

8. A luer connection device comprising:
   a housing including a side wall having an inside surface defining a lumen with a central axis, a proximal end, and a distal end, the side wall comprising a male luer tip, and the lumen having a passageway therethrough providing fluid communication between the proximal end and the distal end;

a central flow diverter configured to extend in a rotational taper towards the central axis of the lumen to direct a fluid to a circumferential dead space distal to the male luer tip, and a flow expansion channel disposed in the side wall of the housing configured to scallop outwardly and partially extending along a longitudinal axis from the distal end toward the proximal end, the flow expansion channel configured to extend in a rotational taper outwardly from the central axis of the lumen, wherein the flow diverter directs fluid flow into the flow expansion channel.

9. The luer connection device of claim 8, wherein the proximal end is removably connected to a vascular access device.

10. The luer connection device of claim 9, wherein the vascular access device is a syringe, an extension set, an intravenous set, a stop cock, tubing, high pressure extension tubing or a needleless connector.

11. The luer connection device of claim 8, wherein the proximal end is integrally connected to a vascular access device.

12. The luer connection device of claim 11, wherein the vascular access device is a syringe, an extension set, an intravenous set, a stop cock, tubing, high pressure extension tubing, or a needleless connector.

13. The luer connection device of claim 12, wherein the syringe is a pre-filled flush syringe.

* * * * *